United States Patent
Morley et al.

(10) Patent No.: US 6,676,684 B1
(45) Date of Patent: Jan. 13, 2004

(54) ROLL-PITCH-ROLL-YAW SURGICAL TOOL

(75) Inventors: Tracey A. Morley, Sunnyvale, CA (US); Daniel T. Wallace, Redwood City, CA (US)

(73) Assignee: Intuitive Surgical, Inc., Mountain View, CA (US)

( * ) Notice: Subject to any disclaimer, the term of this patent is extended or adjusted under 35 U.S.C. 154(b) by 47 days.

(21) Appl. No.: 09/947,214

(22) Filed: Sep. 4, 2001

(51) Int. Cl.[7] ............................................... A61B 17/28
(52) U.S. Cl. ........................................................ 606/205
(58) Field of Search ................................ 606/205, 206, 606/207, 208, 210, 211

(56) References Cited

U.S. PATENT DOCUMENTS

| | | | |
|---|---|---|---|
| 4,762,455 A | 8/1988 | Coughlan et al. | |
| 5,078,140 A | 1/1992 | Kwoh | |
| 5,524,180 A | 6/1996 | Wang et al. | |
| 5,553,198 A | 9/1996 | Wang et al. | |
| 5,562,700 A | * 10/1996 | Huitema et al. | 606/207 |
| 5,667,476 A | * 9/1997 | Frassica et al. | 600/149 |
| 5,695,521 A | * 12/1997 | Anderhub | 606/205 |
| 5,754,741 A | 5/1998 | Wang et al. | |
| 5,762,458 A | 6/1998 | Wang et al. | |
| 5,808,665 A | 9/1998 | Green | |
| 5,810,716 A | 9/1998 | Mukherjee et al. | |
| 5,855,583 A | 1/1999 | Wang et al. | |
| 5,907,664 A | 5/1999 | Wang et al. | |
| 5,919,206 A | * 7/1999 | Gengler et al. | 606/205 |
| 5,931,832 A | 8/1999 | Jensen | |
| 5,964,780 A | * 10/1999 | Balazs | 606/208 |
| 6,132,441 A | 10/2000 | Grace | |
| 6,206,903 B1 | * 3/2001 | Ramans | 606/205 |
| 6,228,083 B1 | * 5/2001 | Lands et al. | 606/50 |

OTHER PUBLICATIONS

*Medical Robotics and Compiter Assisted Surgery*, Second Annual International Symposium, Nov. 4–7, 1995 at the Marriot Inner harbor Hotel, Baltimore, Maryland USA.

* cited by examiner

*Primary Examiner*—Kevin T. Truong
*Assistant Examiner*—Victor X Nguyen
(74) *Attorney, Agent, or Firm*—Townsend and Townsend and Crew LLP

(57) ABSTRACT

A robotic surgical tool includes an elongate shaft having a working end and a shaft axis. A wrist member has a proximal portion pivotally connected to the working end to rotate relative to the working end around a pitch axis which is nonparallel to the shaft axis. An end effector is pivotally mounted on a distal portion of the wrist member to rotate around a wrist roll axis of the wrist member. The wrist roll axis extends between the proximal portion and the distal portion of the wrist member. The end effector is pivotally mounted to rotate relative to the wrist member around a yaw axis which is nonparallel to the wrist roll axis. A torsion tube is coupled with the end effector base and is rotatable to turn the end effector base around the wrist roll axis of the wrist member. The torsion tube extends through an interior of the elongate shaft to a proximal end opposite from the working end of the elongate shaft. The torsion tube is bendable around the pitch axis with rotation of the wrist member around the pitch axis relative to the working end.

24 Claims, 10 Drawing Sheets

ROLL-PITCH-ROLL-YAW SURGICAL TOOL

CROSS-REFERENCES TO RELATED APPLICATIONS

This application is related to the following patents and patent applications, the full disclosures of which are incorporated herein by reference:

PCT International Application No. PCT/US98/19508, entitled "Robotic Apparatus", filed on Sep. 18, 1998, and published as W99/50721;

U.S. patent application Ser. No. 09/418,726, entitled "Surgical Robotic Tools, Data Architecture, and Use", filed on Oct. 15, 1999;

U.S. patent application Ser. No. 60/111,711, entitled "Image Shifting for a Telerobotic System", filed on Dec. 8, 1998;

U.S. patent application Ser. No. 09/378,173, entitled "Stereo Imaging System for Use in Telerobotic System", filed on Aug. 20, 1999;

U.S. patent application Ser. No. 09/398,507, entitled "Master Having Redundant Degrees of Freedom", filed on Sep. 17, 1999;

U.S. application Ser. No. 09/399,457, entitled "Cooperative Minimally Invasive Telesurgery System", filed on Sep. 17, 1999;

U.S. patent application Ser. No. 09/373,678, entitled "Camera Referenced Control in a Minimally Invasive Surgical Apparatus", filed on Aug. 13, 1999;

U.S. patent application Ser. No. 09/398,958, entitled "Surgical Tools for Use in Minimally Invasive Telesurgical Applications", filed on Sept. 17, 1999;

U.S. patent application Ser. No. 09/626,527, entitled "Roll-Pitch-Roll Surgical Tool", filed Jul. 27, 2000; and U.S. Pat. No. 5,808,665, entitled "Endoscopic Surgical Instrument and Method for Use", issued on Sep. 15, 1998.

BACKGROUND OF THE INVENTION

Advances in minimally invasive surgical technology could dramatically increase the number of surgeries performed in a minimally invasive manner. Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch or less) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

There are many disadvantages relating to current minimally invasive surgical (MIS) technology. For example, existing MIS instruments deny the surgeon the flexibility of tool placement found in open surgery. Most current laparoscopic tools have rigid shafts, so that it can be difficult to approach the worksite through the small incision. Additionally, the length and construction of many endoscopic instruments reduces the surgeon's ability to feel forces exerted by tissues and organs on the end effector of the associated tool. The lack of dexterity and sensitivity of endoscopic tools is a major impediment to the expansion of minimally invasive surgery.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation.

While viewing a three-dimensional image of the surgical site on a suitable viewer or display, the surgeon performs the surgical procedures on the patient by manipulating master input or control devices of the workstation. The master controls the motion of a servomechanically operated surgical instrument. During the surgical procedure, the telesurgical system can provide mechanical actuation and control of a variety of surgical instruments or tools having end effectors such as, e.g., tissue graspers, needle drivers, or the like, that perform various functions for the surgeon, e.g., holding or driving a needle, grasping a blood vessel, or dissecting tissue, or the like, in response to manipulation of the master control devices.

Some surgical tools employ a roll-pitch-yaw mechanism for providing three degrees of rotational movement to an end effector around three perpendicular axes. At about 90° pitch, the yaw and roll rotational movements overlap, resulting in the loss of one degree of rotational movement.

SUMMARY OF THE INVENTION

The present invention is generally directed to robotic surgery methods, devices, and systems. The invention provides a minimally invasive surgical tool which operates with three degrees of rotational movement at about 90° pitch. In particular, the surgical tool employs a roll-pitch-roll configuration in which an elongate shaft is rotatable in proximal roll, a wrist member is pivotally mounted on the working end of the elongate shaft to rotate in pitch, and an end effector is pivotally mounted on the wrist member to rotate in distal roll around the wrist roll axis of the wrist member. At about 90° pitch, the wrist roll axis is generally perpendicular to the shaft axis of the elongate shaft. The proximal roll around the shaft roll axis and the distal roll around the wrist roll axis do not generally overlap. In some embodiments, an additional mechanism is used to actuate the end effector in yaw rotation.

In accordance to an aspect of the present invention, a minimally invasive surgical instrument comprises an elongate shaft having a working end and a shaft axis. A wrist member has a proximal portion pivotally connected to the working end to rotate relative to the working end around a pitch axis which is nonparallel to the shaft axis. An end effector is pivotally mounted on a distal portion of the wrist member to rotate around a wrist roll (distal roll) axis of the wrist member. The wrist roll axis extends between the proximal portion and the distal portion of the wrist member. The end effector may also be pivotally mounted to rotate relative to the wrist member around a yaw axis which is nonparallel to the wrist roll axis.

In some embodiments, the end effector includes an end effector base which is pivotally mounted on the distal portion of the wrist member to rotate around the distal wrist roll axis of the wrist member. The end effector includes at least one working member pivotally mounted to the end effector base to rotate around the yaw axis. The yaw axis is perpendicular to the distal wrist roll axis. The pitch axis is perpendicular to the shaft axis.

In specific embodiments, a torsion tube is coupled with the end effector base and is rotatable to turn the end effector base around the wrist roll axis of the wrist member. The torsion tube extends through an interior of the elongate shaft to a proximal end opposite from the working end of the elongate shaft. The end effector includes at least one working member pivotally mounted to the end effector base to rotate around the yaw axis. The working member of the end effector is rotatable around the yaw axis by a yaw pulley-and-cable mechanism including at least one cable extending from the working member of the end effector through an interior of the torsion tube to the proximal end of the elongate shaft. The wrist member is rotatable relative to the working end around the pitch axis by a pitch pulley-and-cable mechanism including at least one cable extending from the wrist member to the proximal end of the elongate shaft through a space inside an interior of the elongate shaft and outside of the torsion tube. The torsion tube is bendable around the pitch axis with rotation of the wrist member around the pitch axis relative to the working end.

In accordance with another aspect of the present invention, a minimally invasive surgical instrument comprises an elongate shaft having a working end and a shaft axis. A wrist member has a proximal portion pivotally connected to the working end to rotate relative to the working end around a pitch axis which is nonparallel to the shaft axis. An end effector is pivotally mounted on a distal portion of the wrist member to rotate around a distal wrist roll axis of the wrist member. The wrist roll (distal roll) axis extends between the proximal portion and the distal portion of the wrist member. A torsion tube is coupled with the end effector and is rotatable to turn the end effector around the wrist roll axis of the wrist member.

In accordance with another aspect of the invention, a method of performing minimally invasive endoscopic surgery in a body cavity of a patient comprises introducing an elongate shaft having a working end into the cavity. The elongate shaft has a proximal end and a shaft axis between the working end and the proximal end. The method further comprises rotating a wrist member pivotally coupled with the working end relative to the working end. The wrist member has a wrist roll axis. An end effector pivotally mounted on the wrist member is rotated around the wrist roll axis to position the end effector at a desired location inside the cavity, by turning a torsion tube extending through an interior of the elongate shaft to the proximal end of the elongate shaft and being coupled with the end effector.

In some method embodiments, the wrist member is rotated around a pitch axis which is perpendicular to at least one of the shaft axis and the wrist roll axis to change an angle between the wrist roll axis and the shaft axis. Rotating the wrist member around the pitch axis bends the torsion tube around the pitch axis. At least one working member of the end effector is rotated around a yaw axis nonparallel to the wrist roll axis. The elongate shaft is rotated around the shaft axis to position the end effector at the desired location inside the cavity.

DESCRIPTION OF THE PREFERRED EMBODIMENTS

Figure 1:
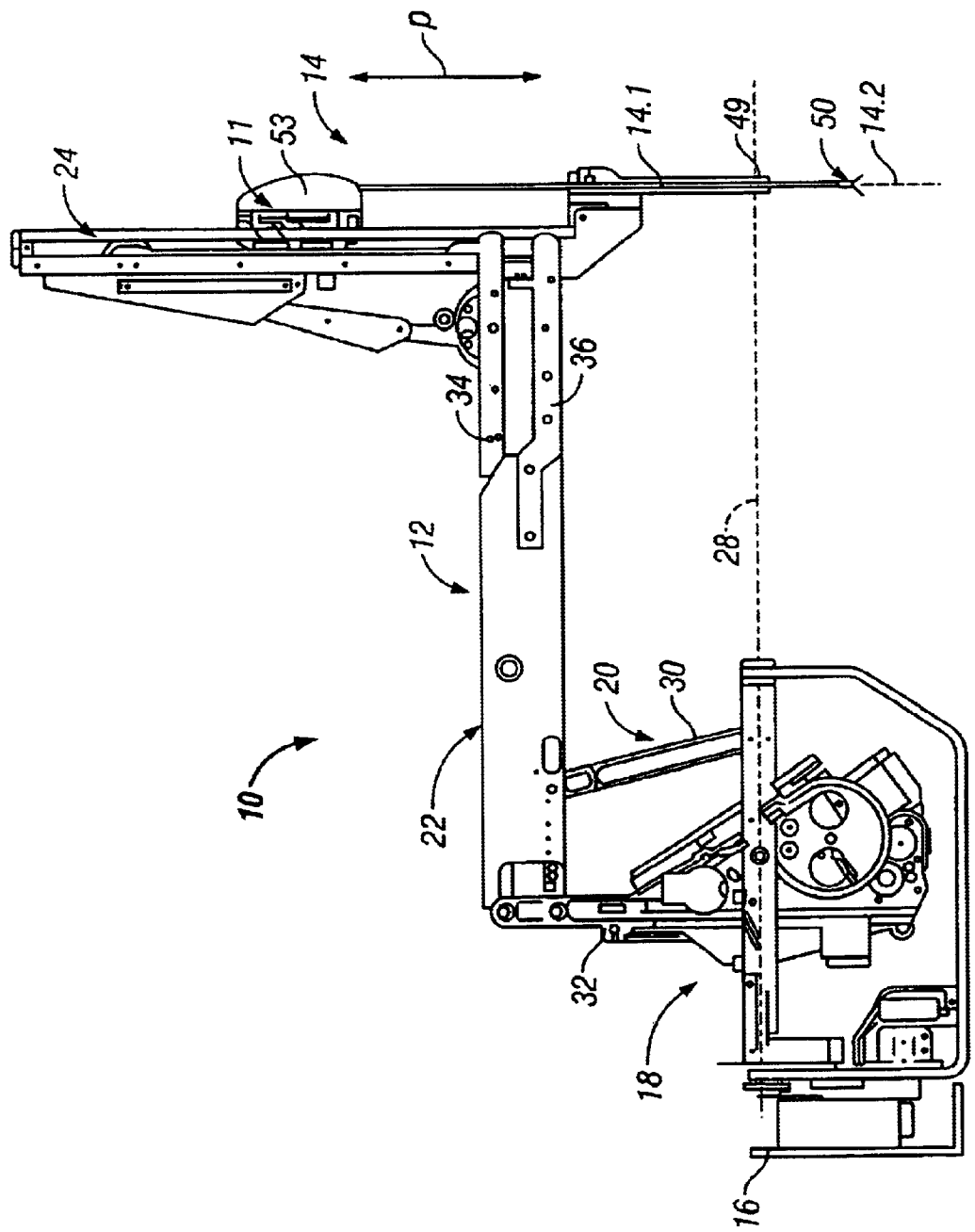
FIG. 1 is a side view of a robotic arm and surgical instrument assembly according to a preferred embodiment of the invention.
Figure 2:
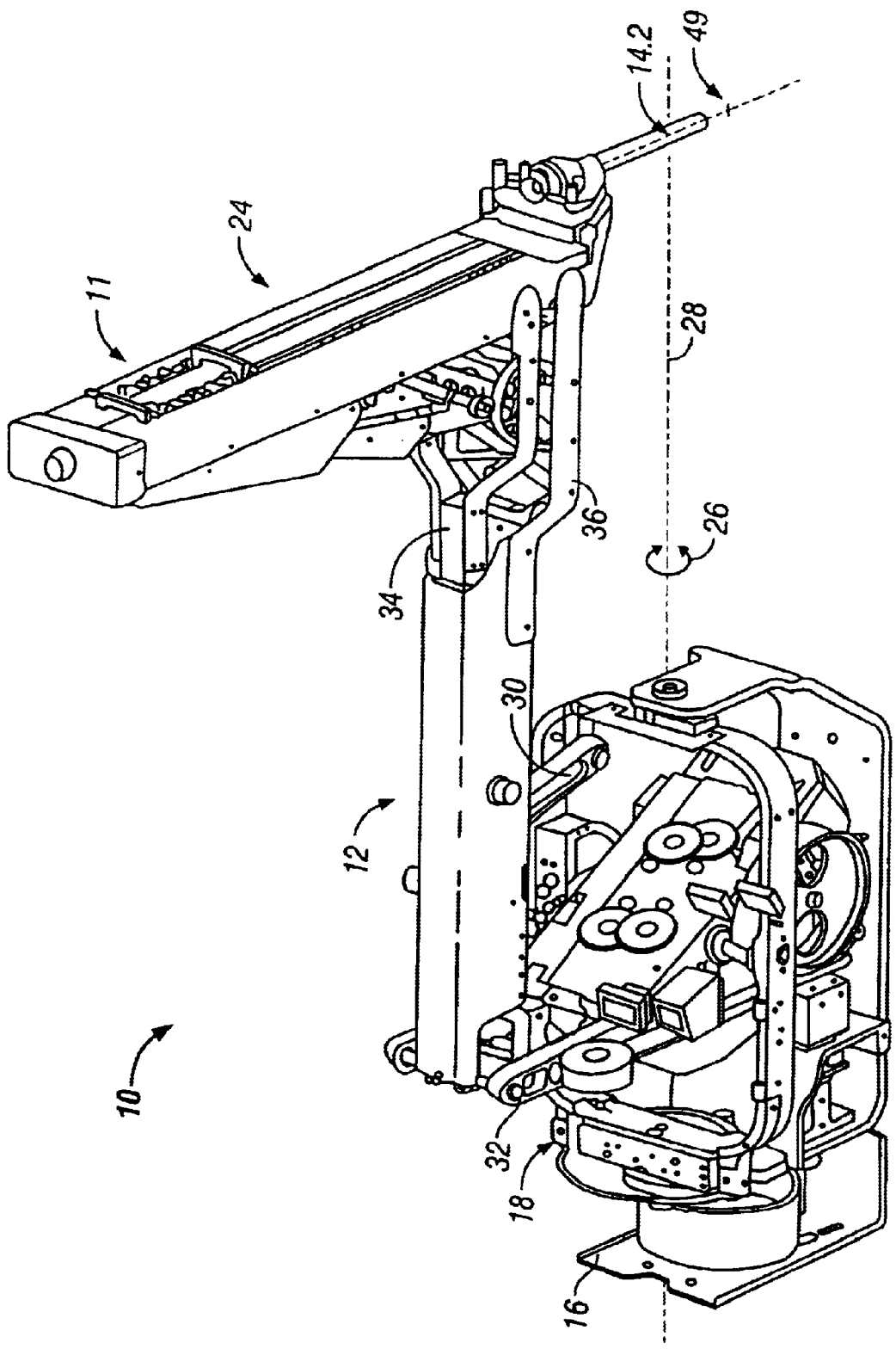
FIG. 2 is a perspective view of the robotic arm and surgical instrument assembly of FIG. 1.
Figure 3:
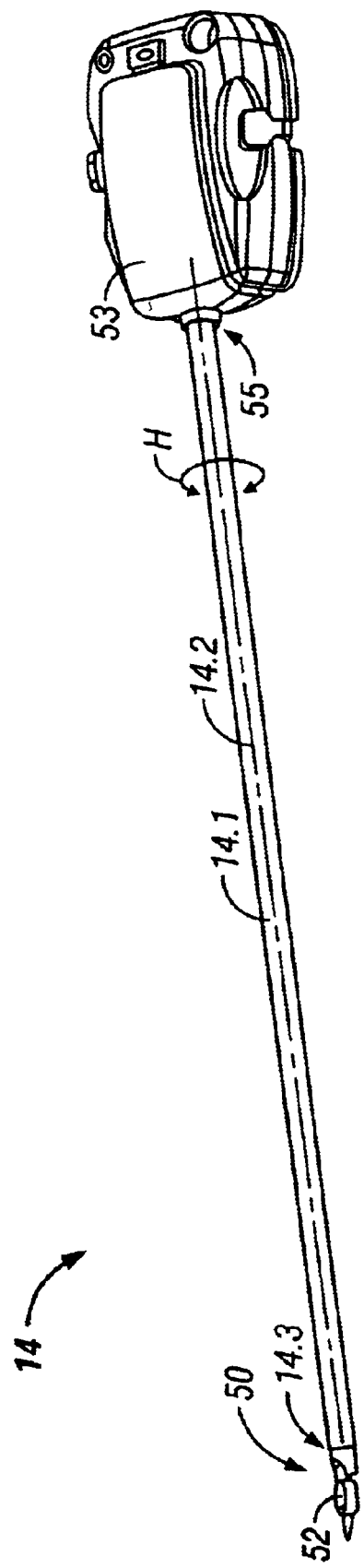
FIG. 3 is a perspective view of a surgical instrument according to a preferred embodiment of the invention.

FIGS. 1 and 2 illustrate an example of a robotic arm and surgical instrument assembly 10. The assembly 10 includes a robotic arm 12 and a surgical instrument 14. FIG. 3 indicates the general appearance of the surgical instrument 14.

The surgical instrument 14 includes an elongate shaft 14.1. A wrist-like mechanism 50 is located at a working end of the shaft 14.1. A housing 53 arranged releasably to couple the instrument 14 to the robotic arm 12 is located at an opposed end of the shaft 14.1. In FIG. 1, and when the instrument 14 is coupled or mounted on the robotic arm 12, the shaft 14.1 extends along an axis indicated at 14.2. The instrument 14 is typically releasably mounted on a carriage 11 which is driven to translate along a linear guide formation 24 in the direction of arrows P. The surgical instrument 14 is described in greater detail herein below.

The robotic arm 12 is typically mounted on a base (not shown) by a bracket or mounting plate 16. The base is typically in the form of a mobile cart or trolley (not shown) which is retained in a stationary position during a surgical procedure.

The robotic arm 12 includes a cradle 18, an upper arm portion 20, a forearm portion 22, and the guide formation 24. The cradle 18 is pivotally mounted on the plate 16 in a gimbaled fashion to permit rocking movement of the cradle in the direction of arrows 26 about a pivot axis 28, as shown in FIG. 2. The upper arm portion 20 includes link members 30, 32 and the forearm portion 22 includes link members 34, 36. The link members 30, 32 are pivotally mounted on the cradle 18 and are pivotally connected to the link members 34, 36. The link members 34, 36 are pivotally connected to the guide formation 24. The pivotal connections between the link members 30, 32, 34, 36, the cradle 18, and the guide formation 24 are arranged to enable the robotic arm to move in a specific manner.

Figure 4:
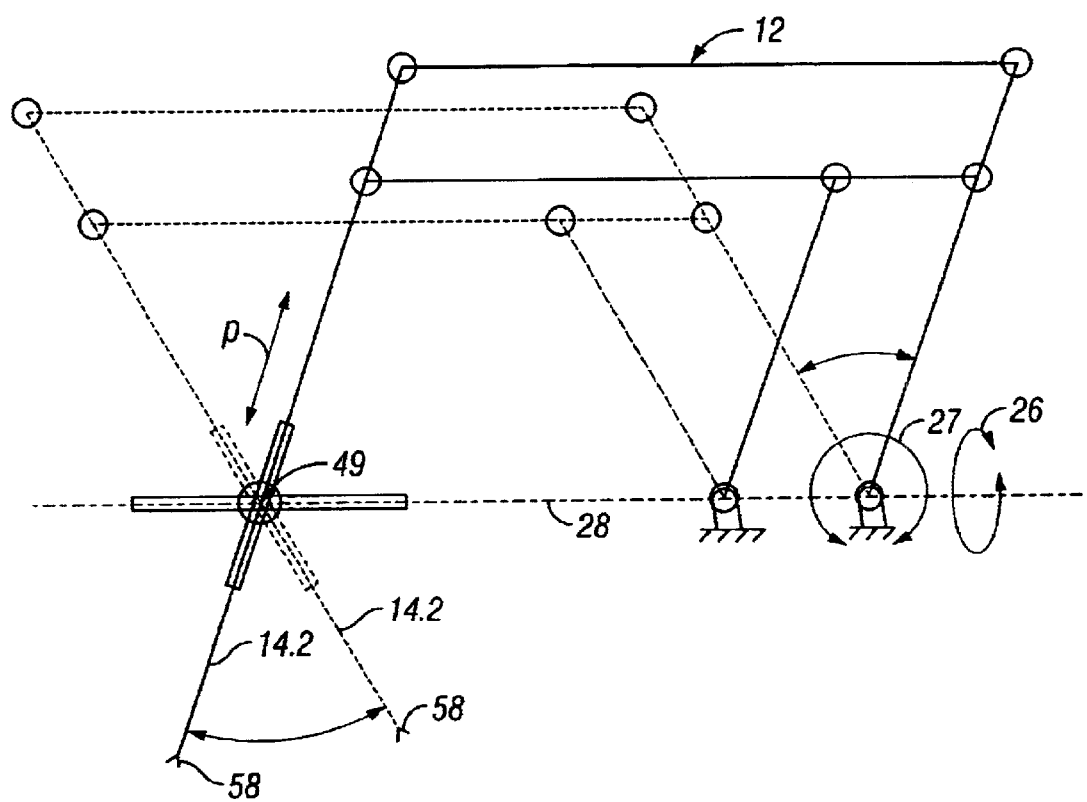
FIG. 4 is a schematic kinematic diagram corresponding to the side view of the robotic arm shown in FIG. 1, and indicates the arm having been displaced from one position into another position.

The movements of the exemplary robotic arm 12 is illustrated schematically in FIG. 4. The solid lines schematically indicate one position of the robotic arm and the dashed lines indicate another possible position into which the arm can be displaced from the position indicated in solid lines.

It will be understood that in a preferred embodiment, the axis 14.2 along which the shaft 14.1 of the instrument 14 extends when mounted on the robotic arm 12 pivots about a pivot center or fulcrum 49. Thus, irrespective of the movement of the robotic arm 12, the pivot center 49 normally remains in substantially the same position relative to a stationary cart on which the arm 12 is mounted. In use, the pivot center 49 is typically positioned at a port of entry into a patient's body during an endoscopic procedure when an internal surgical procedure is to be performed. It will be appreciated that the shaft 14.1 extends through such a port of entry, the wrist-like mechanism 50 then being positioned inside the patient's body. Thus, the general position of the mechanism 50 relative to the surgical site in a patient's body can be changed by movement of the arm 12. Since the pivot center 49 is coincident with the port of entry, such movement of the arm does not excessively effect the surrounding tissue at the port of entry. It is to be appreciated that the field of application of the invention is not limited to surgical procedures at internal surgical sites only, but can be used on open surgical sites as well.

As can best be seen in FIG. 4, the robotic arm 12 provides three degrees of freedom of movement to the surgical instrument 14 when mounted thereon. These degrees of freedom of movement are firstly the gimbaled motion indicated by arrows 26, pivoting or pitching movement as indicated by arrows 27, and the linear displacement in the direction of arrows P. Movement of the arm as indicated by arrows 26, 27 and P is controlled by appropriately positioned actuators, e.g., electrical motors or the like, which respond to inputs from its associated master control to drive the arm 12 to a desired position as dictated by movement of the master control.

It should be understood that although the exemplary arm 12 illustrated in FIGS. 1–4 has a mechanically constrained center or pivot 49, the surgical instruments of the present invention may be employed with other types of robotic arms, such as natural center arms, computed center arms, and the like.

Roll-Pitch-Yaw Mechanism

Figure 7:
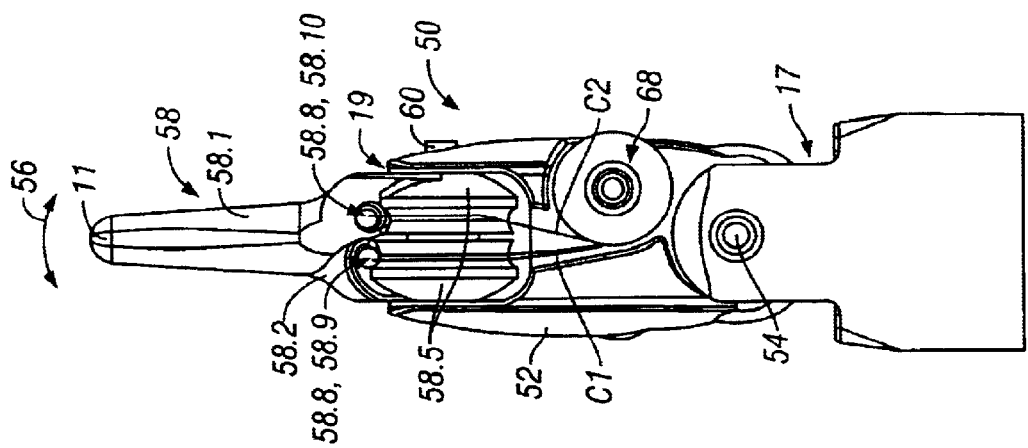
FIG. 7 is a side view of the wrist mechanism of FIG. 5 along arrow VII.
Figure 6:
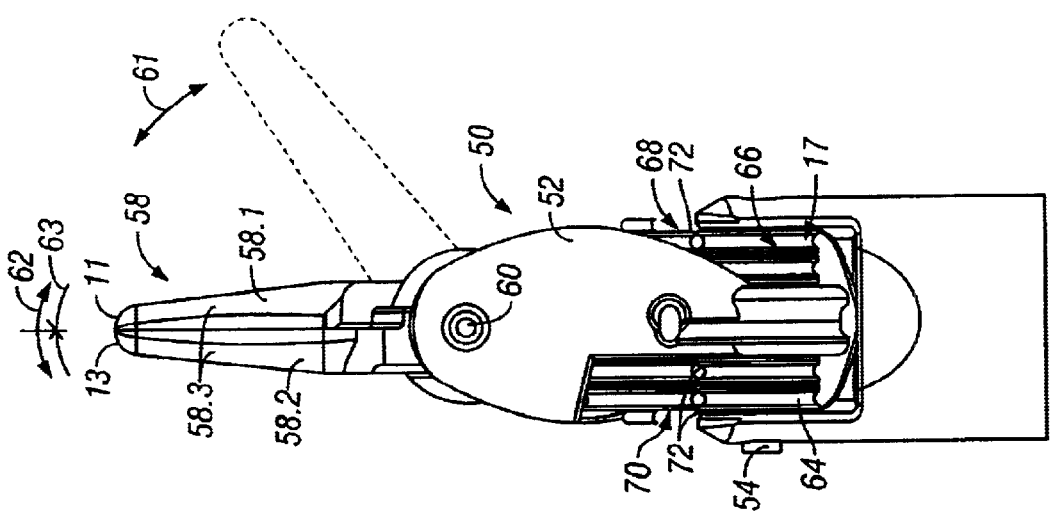
FIG. 6 is a front view of the wrist mechanism of FIG. 5 along arrow VI.
Figure 5:
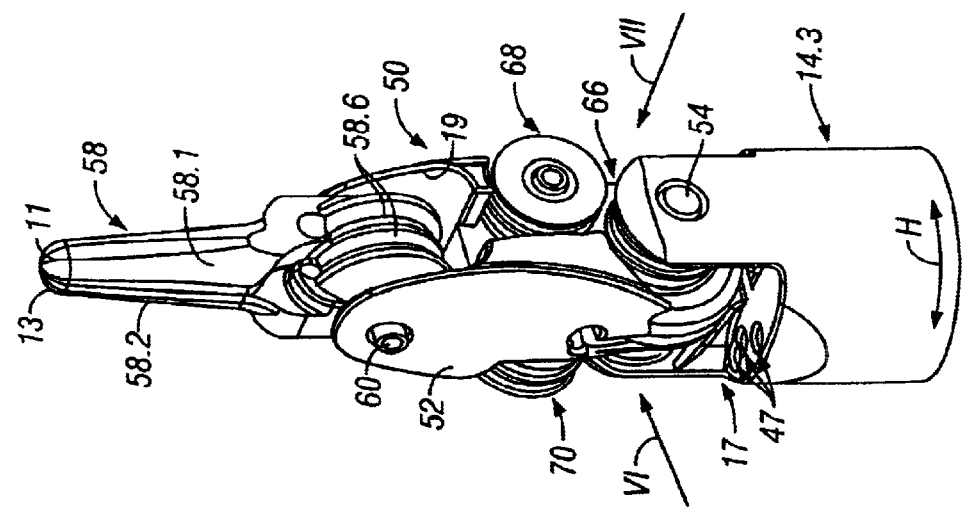
FIG. 5 is a perspective view of a roll-pitch-yaw wrist mechanism.

FIGS. 5, 6 and 7 show a roll-pitch-yaw wrist-like mechanism 50. In FIG. 5, the working end of the shaft 14.1 is indicated at 14.3. The wrist-like mechanism 50 includes a rigid wrist member 52. One end portion of the wrist member 52 is pivotally mounted in a clevis 17 on the end 14.3 of the shaft 14.1 by means of a pivotal connection 54. As best seen in FIG. 7, the wrist member 52 can pitch in the direction of arrows 56 about the pivotal connection 54. This rotation around the pivotal connection 54 in the direction 56 is referred to as the pivot or pitch of the wrist member 52. The end 14.3 is rotatable with the shaft 14.1 around the axis 14.2 in the direction H, as shown in FIGS. 3 and 5. This rotation around the axis 14.2 in the direction H is referred to as the roll of the working end 14.3.

An end effector, generally indicated by reference numeral 58, is pivotally mounted on an opposed end of the wrist member 52. The end effector 58 is in the form of forceps or graspers for grasping tissue or the like during a surgical procedure. Accordingly, the end effector 58 has two parts 58.1, 58.2 together defining ajaw-like arrangement. The end effector 58 is pivotally mounted in a clevis 19 on an opposed end of the wrist member 52, by means of a pivotal connection 60. Free ends 11, 13 of the parts 58.1, 58.2 are angularly displaceable about the pivotal connection 60 toward and away from each other as indicated by arrows 62, 63 in FIG. 6. This movement of the parts 58.1, 58.2 is referred to as the grip of the end effector 58. The members 58.1, 58.2 can be displaced angularly about the pivotal connection 60 to change the orientation of the end effector 58 as a whole, relative to the wrist member 52. Thus, each part 58.1, 58.2 is angularly displaceable about the pivotal connection 60 independently of the other, so that the end effector 58 is, as a whole, angularly displaceable about the pivotal connection 60 in the direction 61, as indicated in dashed lines in FIG. 6. This rotation around the pivotal connection 60 in the direction 61 is referred to the yaw of the end effector 58. The wrist mechanism 50 as illustrated in FIGS. 5–7 is referred to as a roll-pitch-yaw mechanism having roll in the direction H, pitch in the direction 56, and yaw in the direction 61.

The parts 58.1, 58.2 each include an elongate finger portion or end effector element 58.3 and an end effector mounting formation in the form of, e.g., a pulley portion 58.5. In a preferred embodiment, the finger portion 58.3 is integrally formed with the pulley portion 58.5. The pulley portion 58.5 defines a circumferentially extending channel 58.6 in which an elongate element in the form of, e.g., an activation cable, is carried. A generally circumferentially directed hole 58.8 extends through a nape region of the finger portion 58.3 and generally in register with the circumferentially extending channel 58.6. The hole 58.8 has a first portion 58.9 and a second portion 58.10 having a diameter greater than the first portion 58.9. In use, the activation cable has a thickened portion along its length which seats in the hole portion 58.10, the rest of the activation cable then extending along the channel 58.6 in opposed directions. The thickened portion is crimped in its seated position in the hole portion 58.10 so as to anchor the cable in the hole 58.8. It will be appreciated that a greater force is necessary to clamp the free ends together when gripping an object therebetween, than that which is required to open the free ends 11, 13. Thus, the thickened portion of the cable is urged against an annular stepped surface between the hole portion 58.9 and the hole portion 58.10, when the free ends 11, 13 are urged into a closed condition.

As best seen in FIG. 6, the wrist member 52 is flanked by two sets of pulleys 64, 66 which are coaxially positioned on the pivotal connection 54 and in the clevis 17 at the end 14.3 of the shaft 14.1. Two further sets of pulleys 68, 70 are rotatably mounted on opposed sides of the wrist member 52. Each pulley of the set of pulleys 68 on the one side of the wrist member 52 is generally co-planar with an associated pulley of the pulley set 66. Furthermore, each of the pulleys 68 is positioned such that its circumference is in close proximity to the circumference of its associated pulley of the pulley set 66. A similar arrangement exists for each pulley of the pulley set 70 on the other side of the wrist member and its associated pulley of the pulley set 64. Thus, the circumferentially extending channel formation of each pulley of the pulley sets 68, 70 and their associated pulleys of the pulley sets 64, 66 define between each of them a space 72 through which an activation cable can snugly pass.

A plurality of elongate elements, e.g., cables, are used to effect movement of the wrist mechanism 50 and end effector 58. As seen in FIG. 7, two cables C1, C2 are anchored on the parts 58.1, 58.2, respectively, to effect movement of the parts 58.1, 58.2 independently in directions 62, 63 or as a whole (FIG. 6).

Cable C1 rides over an outer pulley of the pulley set 64, an outer pulley of the pulley set 70, over part of circumferential channel 58.6 of the pulley portion 58.5 of the part 58.2 of the end effector 58, through the hole 58.8, again along part of the circumferential channel 58.6 of the pulley portion 58.5, over an outer pulley of the pulley set 68 and over an outer pulley of the pulley set 66. Similarly, cable C2 rides over an inner pulley of the pulley set 64, over an inner pulley of the pulley set 70, along the circumferential channel 58.6 of the part 58.1 of the end effector 58, through the hole 58.8 of the part 58.1, again along the circumferential channel 58.6 of the pulley portion 58.5, over an inner pulley of the pulley set 68 and over an inner pulley of the pulley set 66. The cables C1, C2 pass from the wrist mechanism 50 through appropriately positioned holes 47 in the base region of the clevis 17 (FIG. 5), and internally along the shaft 14.1, toward the housing 53 (FIG. 3). The housing 53 includes driving members, e.g., in the form of spool assemblies for manipulating the cables. Additional details of the spool assemblies and the grip mechanism for manipulating the finger portions 58.1, 58.2 to achieve gripping as well as description of various surgical tools can be found in U.S. patent application Ser. No. 09/398,958, entitled "Surgical Tools for Use in Minimally Invasive Telesurgical Applications", filed on Sep. 17, 1999.

Figure 8:
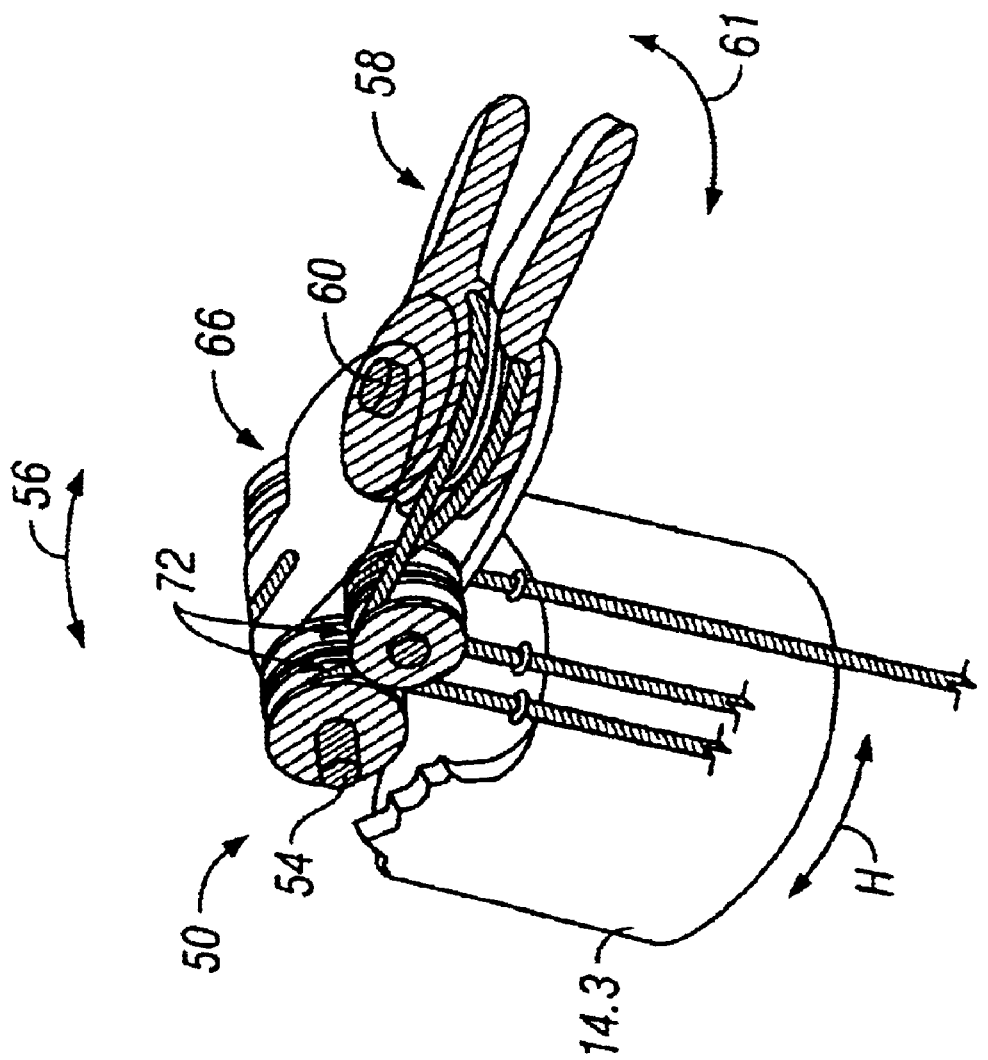
FIG. 8 is a perspective view of the wrist mechanism of FIG. 5 schematically illustrating the singularity at the 90° pitch position.

When the end effector 58 is oriented forward, the roll, pitch, and yaw provide rotational movements relative to three generally perpendicular axes. FIG. 8 shows the position of the end effector 58 after rotation in pitch in the direction 56 of the wrist member 52 around the pivotal connection 54 by about 90°. In this position, the yaw in the direction 61 around the pivotal connection 60 overlaps with the roll H of the working end 14.3. The overlap or redundancy results in the loss of one degree of freedom of movement of the end effector 58 at or near this position of singularity. In some applications, the end effector 58 may be used primarily at this position of about 90° pitch. It is desirable to provide a wrist mechanism that does not operate at a singularity in this position.

Roll-Pitch-Roll-Yaw Mechanism

Figure 9:
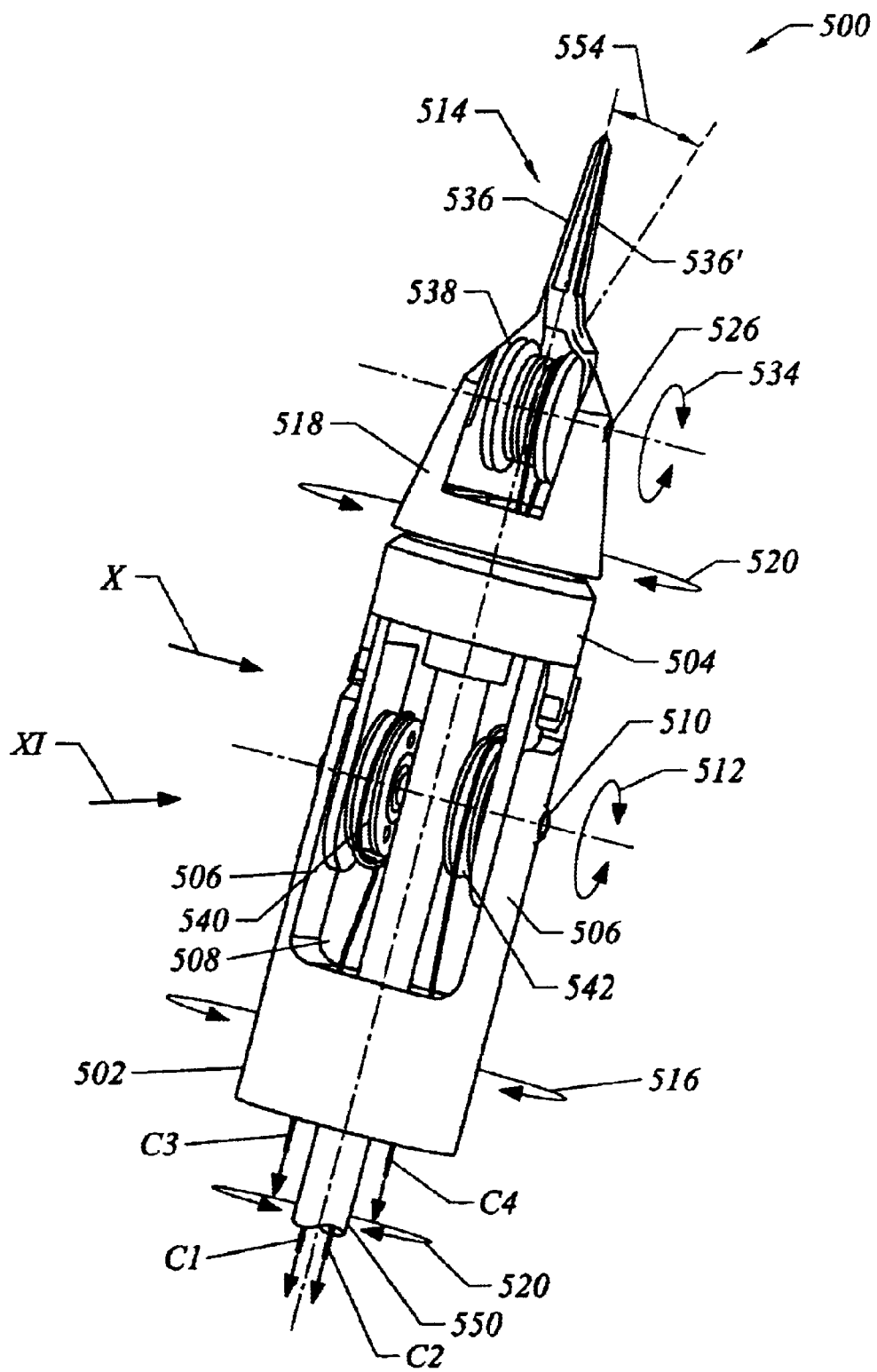
FIG. 9 is a perspective view of a roll-pitch-roll-yaw wrist mechanism according to a preferred embodiment of the present invention.
Figure 10:
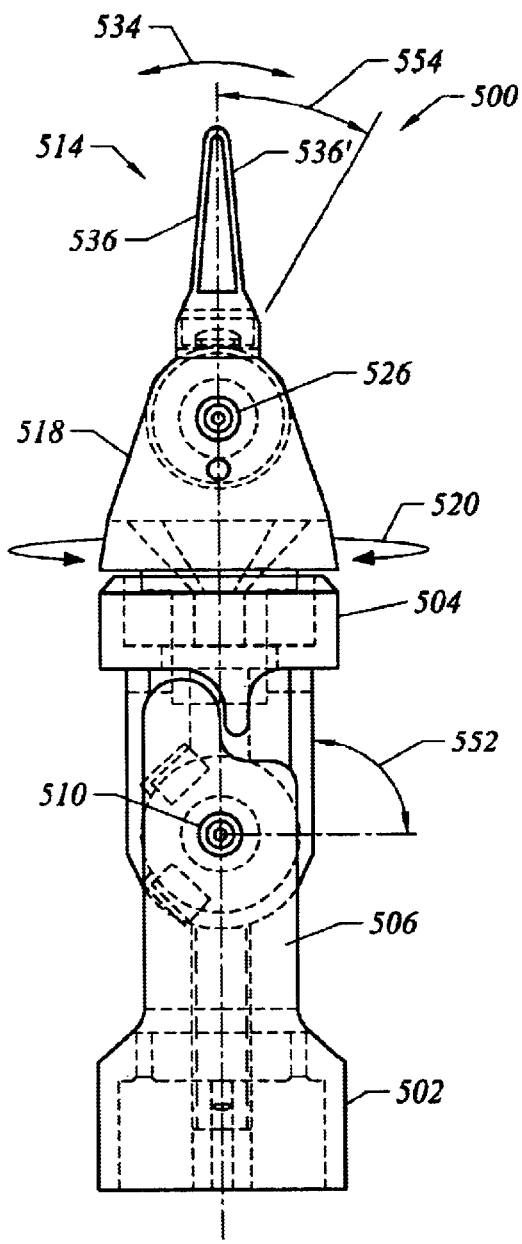
FIG. 10 is a side view of the wrist mechanism of FIG. 9 along arrow X without showing the activation elements for manipulating the wrist mechanism.
Figure 11:
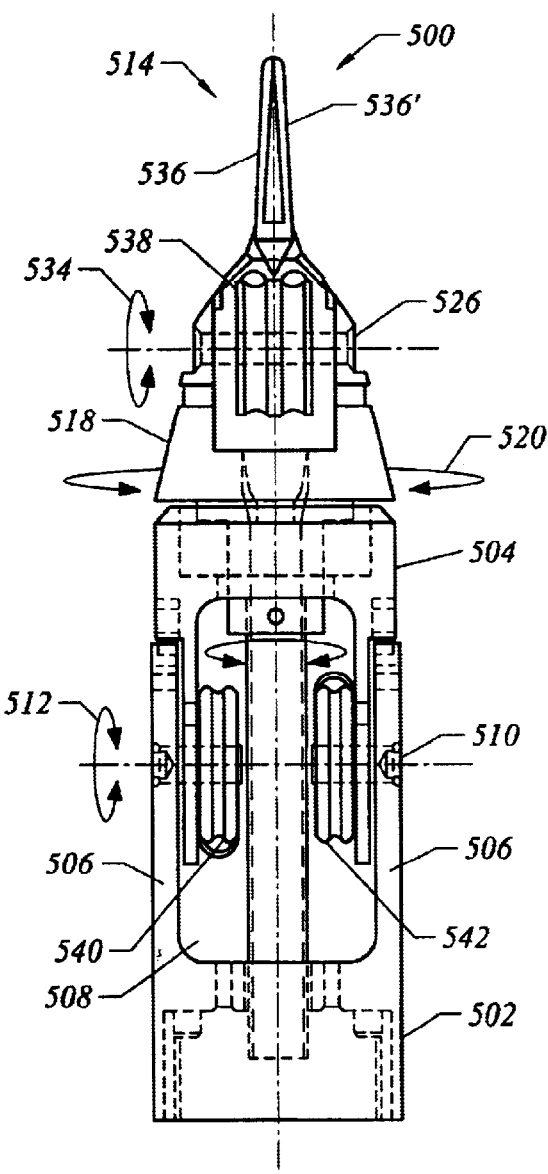
FIG. 11 is a front view of the wrist mechanism of FIG. 9 along arrow XI without showing the activation elements for manipulating the wrist mechanism.

FIGS. 9–13 show an example of a roll-pitch-roll-yaw wrist-like mechanism 500. In FIG. 9, the working end of the tool shaft is indicated at 502, and includes a pair of extensions 506. The wrist-like mechanism 500 includes a rigid wrist member 504. The extensions 506 of the working end 502 of the tool shaft form a clevis 508 in which one end portion of the wrist member 504 is pivotally mounted by means of a pivotal connection 510. As best seen in FIGS. 9 and 11, the wrist member 504 can pitch in the direction of arrows 512 about the pivotal connection 510 ("pitch axis"). This rotation around the pivotal connection 510 in the direction 512 is referred to as the pivot or pitch of the wrist member 504. The working end 502 is rotatable with the tool shaft around the shaft axis in the direction 516, as shown in FIG. 9. This rotation around the shaft axis ("proximal roll axis") in the direction 516 is referred to as the roll (or proximal roll) of the working end 502.

An end effector, generally indicated by reference numeral 514, is supported on an end effector support base 518 which is pivotally mounted on an opposed end of the wrist member 504 to rotate around its axis ("wrist roll axis" or "distal roll axis") in the direction 520 as shown in FIGS. 9–11. In the embodiment shown, the axis of the base 518 coincides with the axis of the wrist member 504. The rotation in the direction 520 is referred to as the distal roll of the end effector 514. This distal roll of the end effector 514 in the direction 520 is differentiated from the proximal roll of the working end 502 in the direction 516. In the particular position of the wrist mechanism 500 as shown in FIGS. 9–11, the distal roll 520 of the end effector 514 overlaps with the proximal roll 516 of the working end 502. Because the rotation of the wrist member 504 around the pivotal connection 510 provides pitch 512 of the end effector 514, the distal roll 520 generally will not coincide with the proximal roll 516. The wrist mechanism 500 as illustrated in FIGS. 9–11 is referred to as a roll-pitch-roll mechanism.

The exemplary end effector 514 is in the form of forceps or graspers having two parts 536, 536' in a jaw-like arrangement for grasping tissue or the like during a surgical procedure. The part 536' of the end effector 514 is angularly displaceable about the pivotal connection 526 as indicated by arrows 534 in FIGS. 9 and 10. This movement is referred to as the yaw of the end effector 514. In the position of the wrist mechanism 500 as shown in FIGS. 9–11, the yaw 534 of the end effector 514 overlaps with the pitch 512 of the wrist member 504. Because the rotation of the base 518 provides distal roll 520 of the end effector 514, the yaw 534 generally will not coincide with the pitch 512. With the degrees of freedom in proximal roll 516, pitch 512, distal roll 520, and yaw 534 in the specific embodiment shown, the wrist mechanism 500 as illustrated in FIGS. 9–11 is referred to as a roll-pitch-roll-yaw mechanism.

Figure 12:
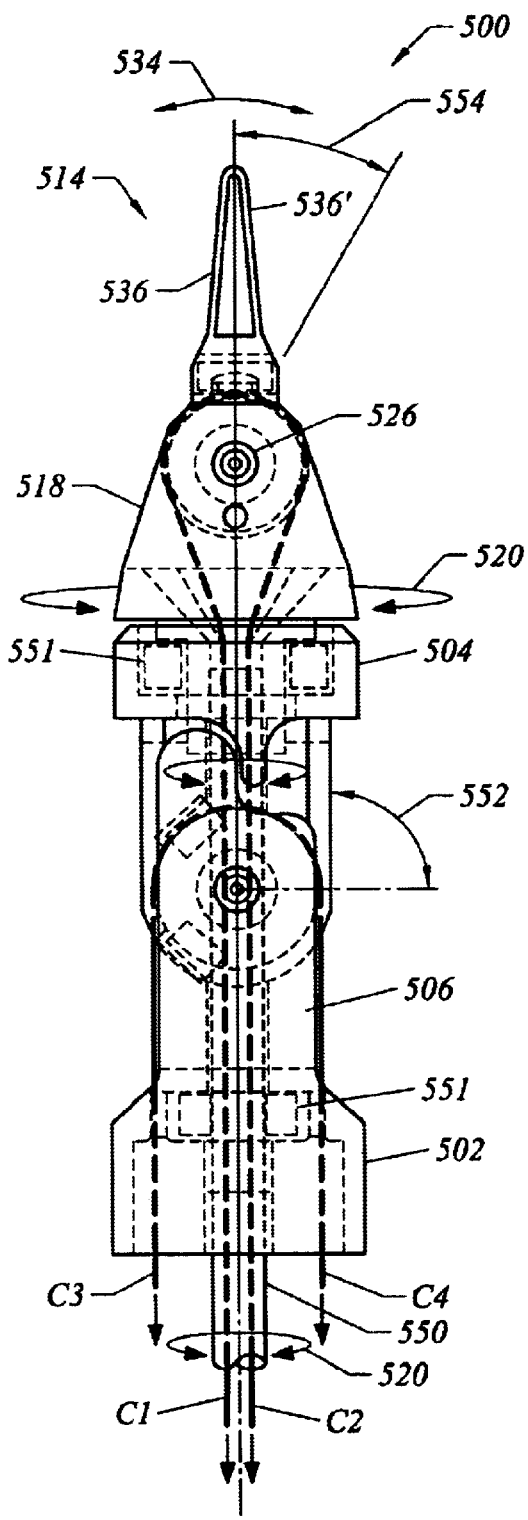
FIG. 12 is a side view of the wrist mechanism of FIG. 9 along arrow X illustrating the activation cables and torsion tube for manipulating the wrist mechanism.
Figure 13:
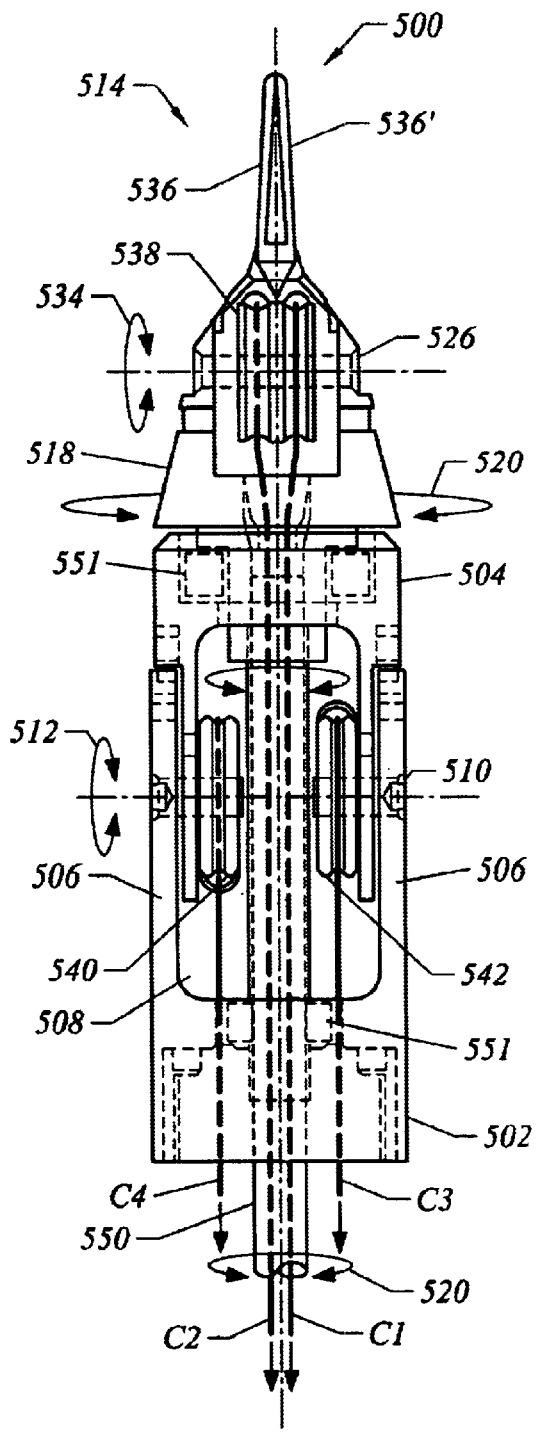
FIG. 13 is a front view of the wrist mechanism of FIG. 9 along arrow XI illustrating the activation cables and torsion tube for manipulating the wrist mechanism.

The end effector 514 includes an elongate finger portion or end effector element including the pair of working elements 536, 536', and an end effector mounting formation in the form of, e.g., a pulley portion 538. The finger portion may be integrally formed with the pulley portion 538. The pulley portion 538 defines a pair of circumferentially extending channels for receiving one or more actuation members. As shown in FIGS. 9, 12, and 13, two elongate members such as activation cables C1, C2 are used to effect movement of the end effector 514 in yaw 534. The end of activation cable C1 is fixed to one circumferentially extending channel and wrapped partially around the channel in one direction, while the end of activation cable C2 is fixed to the other circumferentially extending channel and wrapped partially around the channel in the opposite direction. The cables C1, C2 pass from the wrist mechanism 500 internally through the shaft 14.1 toward the housing 53 (FIG. 3). In a preferred embodiment, the ends of cables C1, C2 are connected in the housing 53 and form a single cable loop. The single cable substantially does not change in length during yaw 534 so that tensioning device, such as a spring or similar member, may optionally be eliminated.

In the specific embodiment shown, the working element 536 is fixed while the working element 536' is movable in yaw by the cables C1, C2 to create gripping action. Alternatively, a two-member end effector similar to that shown in FIGS. 5–7 may be used. In that case, the pulley portion can be configured in a manner similar to the pulley portion 58.5 in the end effector 58 of FIGS. 5–7, and the configuration and operation of the two parts will be similar to those of the parts 58.1, 58.2 in FIGS. 5–7. In yet another embodiment, the end effector 514 may include a single-member working element such as blade or the like.

The end portion of the wrist member 504 disposed in the clevis 508 of the working end 502 includes a pair of pulleys 540, 542. The pulleys 540, 542 are coaxially positioned on the pivotal connection 510. The pitch 512 of the wrist member 504 about the pivotal connection 510 relative to the working end 502 is actuated by elongate members or activation cables C3, C4, as shown in FIGS. 9, 12, and 13. The cable C3 is anchored to a circumferentially extending channel of the pulley 540 and wrapped partially around the channel in one direction. The cable C4 is anchored to a circumferentially extending channel of the pulley 542 and wrapped partially around the channel in the opposite direction. The cables C3, C4 pass from the wrist mechanism 500 internally through the shaft 14.1 toward the housing 53 (FIG. 3). In a preferred embodiment, the cables C3, C4 are connected in the housing 53 and form a single looped cable. The single cable substantially does not change in length during pitch 512 so that no tensioning spring or similar member is needed.

The distal roll 520 of the end effector 514 relative to the wrist member 504 is actuated using a torsion tube 550 connected to the end effector 514, as shown in FIGS. 9, 12, and 13. The torsion tube 550 extends through the center region of the wrist mechanism and shaft 14.1 toward the housing 53 (FIG. 3). A plurality of bearings 551 are provided to support the torsion tube 550 in rotation relative to the wrist member 504 and the working end 502. The torsion tube 550 is configured to bend around the pivotal connection 510 in pitch 512 when the wrist member 504 rotates around the pivotal connection 510 relative to the working end 502. The torsion tube 550 may be made of, for example, a multiple layer spring coil tube with layers wound in opposed directions, such as those conventionally used in odometer cables. Conveniently, the torsion tube 550 has a hollow interior that provides a passage for the cables C1, C2, thereby separating the cables C1, C2 from the cables C3, C4 which are disposed between the torsion tube 550 and the shaft 14.1.

After rotation in pitch 512 of the wrist member 504 around the pivotal connection 510 by about 90°, there is no overlap among the proximal roll 516, pitch 512, and distal roll 520, which are oriented around axes that are generally perpendicular to each other, making the wrist mechanism 500 more suitable to operate in the 90° pitch position than the wrist mechanism 50 of FIGS. 5–8.

As shown in FIG. 12, the wrist mechanism 500 may be configured to limit the pitch 512 to a specific angular range 552, and the end effector 514 may be configured to limit the yaw 534 to a specific angular range 554. In a specific example, the pitch range 552 is about ±90°, and the yaw range 554 is about 0–30°. The torsion tube 550 may also be configured to limit the distal roll to a specific range of, e.g., about ±270°.

Figure 14:
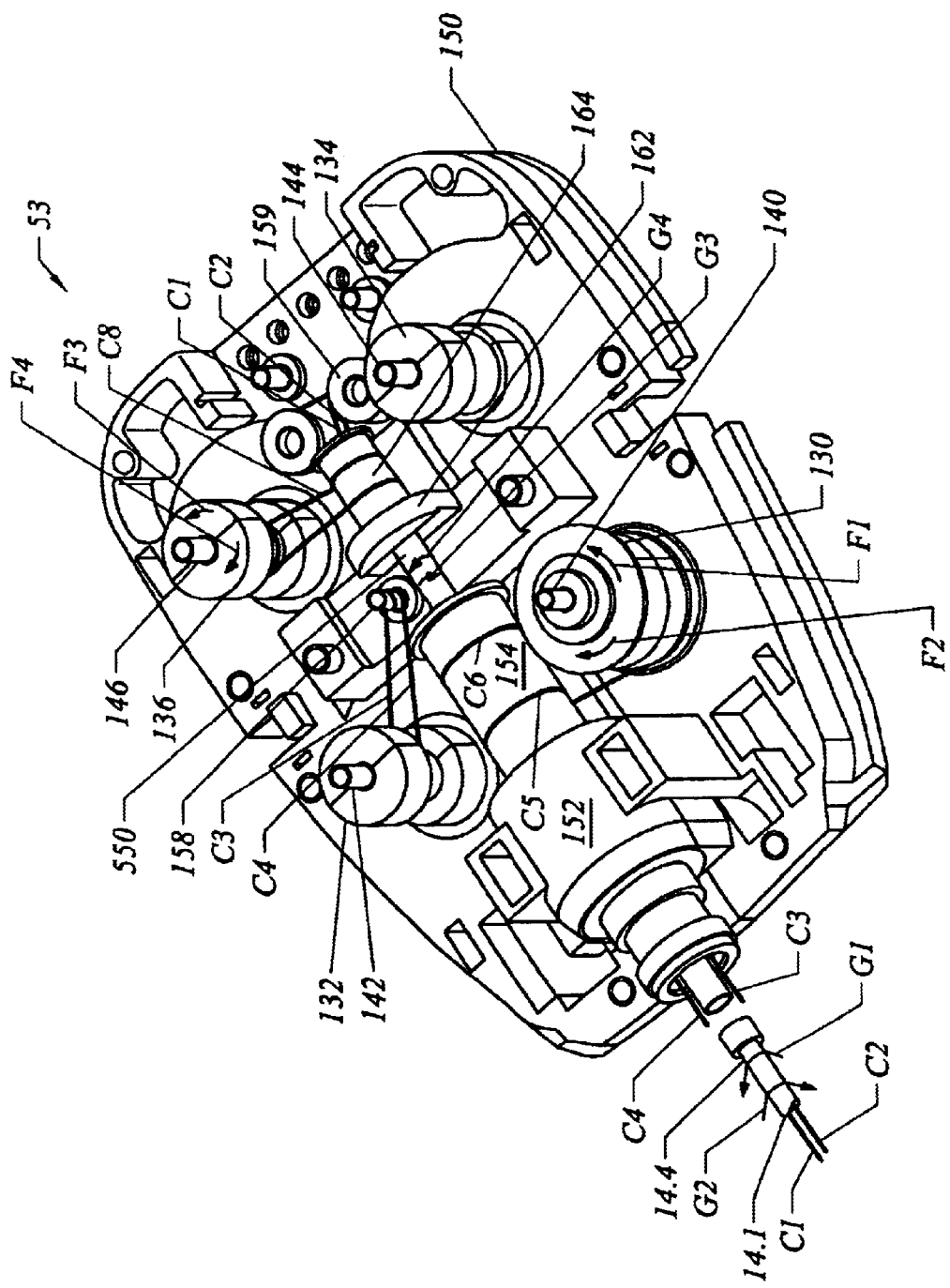
FIG. 14 is a perspective view of the working elements inside the housing of the surgical instrument of FIG. 3.

FIG. 14 shows the working elements inside the housing 53 of the surgical instrument 14 of FIG. 3. The spools are generally indicated by reference numerals 130, 132, 134 and 136, respectively. The spools 130, 132, 134 and 136 are secured on shafts 140, 142, 144 and 146, respectively. The shafts 140, 142, 144, 146 extend through abase 150 of the housing 53. Ends of the shafts 140, 142, 144, 146 are rotatably held in an upper mounting plate, which has been removed from FIG. 14 to show the spools 130, 132, 134 and 136 more clearly. Opposed ends of the shafts 140, 142, 144, 146 extend through the base 150 to an opposed side. At the opposed side, each shaft 140, 142, 144, 146 carries an engaging member (not shown) on its opposed end. Each engaging member is arranged releasably to couple with a complementary engaging member rotatably mounted on the carriage 11, as can best be seen in FIGS. 1 and 2 of the drawings. The engaging members on the carriage 11 are operatively connected to actuators, e.g., electric motors (not shown), to cause selective angular displacement of each engaging member on the carriage in response to actuation of its associated actuator. Thus, selective actuation of the actuators is transmitted through the engaging members on the carriage 11, to the engaging members on the opposed ends of the shafts 140, 142, 144, 146 to cause selective angular displacement of the spools 130, 132, 134, 136.

For manipulating the proximal roll 516, an opposed end portion 14.4 of the shaft 14.1 is rotatably mounted on the base 150 in a bearing assembly 152. Furthermore, the opposed end portion 14.4 of the shaft 14.1 carries a drum 154 which intrudes into the housing 53 beyond the bearing assembly 152. Two elongate elements in the form of activation cables C5, C6 extend between the drum 154 and the spool 130. It will be appreciated that ends of the cables C5, C6 are anchored on the spool 130 and opposed ends are anchored on the drum 154, opposed end portions of the cables C5, C6 being at least partially wrapped around the spool 130 and the drum 154, respectively. Accordingly, angular displacement of the spool 130 in the direction of arrow F1 causes angular displacement of the shaft in the direction of arrow G1, and likewise angular displacement of the spool 130 in the direction of arrow F2 cause angular displacement of the shaft in the direction of arrow G2. The drum 154 and the spool 130 typically have circumferentially extending guide channels to guide wrapping of the cables C5, C6 thereon so as to inhibit the cables C5, C6 from riding over themselves or each other.

Opposed ends of the cables C3, C4 are secured on the spool 132 for manipulating the pitch 512. From the spool 132, the cables C3, C4 are guided over two idler pulleys arranged one on top of the other at 158, and into a centrally disposed passage extending through the drum 154 and into the hollow shaft 14.1. It will be appreciated that selective angular displacement of the spool 132 causes selective pulling of the cables C3, C4. Naturally selective angular displacement of the spool 132 is caused by an actuator, e.g., an electric motor, selectively driving an associated engaging member on the carriage 11 which selectively drives the engaging member on the opposed end of the shaft 142.

For manipulating the yaw 534, opposed ends of the cables C1, C2 are secured on the spool 134. From the spool 134, the cables C1, C2 are guided over two idler pulleys arranged one on top of the other at 159, and into a centrally disposed passage extending through the torsion tube 550. It will be appreciated that selective angular displacement of the spool 134 causes selective pulling of the cables C1, C2. Naturally selective angular displacement of the spool 134 is caused by an actuator, e.g., an electric motor, selectively driving an associated engaging member on the carriage 11 which selectively drives the engaging member on the opposed end of the shaft 142.

For manipulating the distal roll 520, the torsion tube 550 is rotatably mounted on the base 150 in a bearing assembly 162. Furthermore, the torsion tube 550 carries a drum 164 which intrudes into the housing 53 beyond the bearing assembly 162. Two elongate elements in the form of activation cables C7, C8 extend between the drum 164 and the spool 136. It will be appreciated that ends of the cables C7, C8 are anchored on the spool 136 and opposed ends are anchored on the drum 164, opposed end portions of the cables C7, C8 being at least partially wrapped around the spool 136 and the drum 164, respectively. Accordingly, angular displacement of the spool 136 in the direction of arrow F3 causes angular displacement of the shaft in the direction of arrow G3, and likewise angular displacement of the spool 136 in the direction of arrow F4 cause angular displacement of the shaft in the direction of arrow G4. The drum 164 and the spool 136 typically have circumferentially extending guide channels to guide wrapping of the cables C7, C8 thereon so as to inhibit the cables C7, C8 from riding over themselves or each other.

A tensioning arrangement is provided on each spool 130, 132, 134, 136 to tension its associated cable lengths. Examples of the tensioning arrangement can be found, for instance, in U.S. patent application Ser. No. 09/398,958, entitled "Surgical Tools for Use in Minimally Invasive Telesurgical Applications", filed on Sept. 17, 1999.

It will be appreciated that the cables C3 and C4 can form opposed end portions of a single cable, a generally centrally disposed portion of which is wrapped around its associated spool. The same applies to the cables C1 and C2.

It will be appreciated that when the shaft 14.1 is caused to displace angularly relative to the housing 53, the wrist mechanism 52 displaces angularly relative to the housing in sympathy with the shaft 14.1. Thus, the cables C1, C2, C3 and C4 are caused to twist along their lengths during such angular displacement of the shaft 14.1. It has been found that cables made of Tungsten provide sufficient strength, durability and bending properties where the cables C1, C2, C3 and C4 are wrapped around the spools and where they extend over the respective pulleys shown in FIGS. 9, 12, and 13. Moreover, to inhibit stretching of the cables along their lengths and along the shaft 14.1, elongate relatively rigid members, e.g., hypotube portions, are used. Ends of the Tungsten cable portions are typically crimped in the ends of the hypotubes. The hypotubes are typically hollow tubes having a cross-sectionally circular profile.

The above-described arrangements of apparatus and methods are merely illustrative of applications of the principles of this invention and many other embodiments and modifications may be made without departing from the spirit and scope of the invention as defined in the claims. For instance, different actuation mechanisms other than activating cables may be used to manipulate the wrist member, the end effector, the torsion tube, and other components of the surgical instrument. The scope of the invention should, therefore, be determined not with reference to the above description, but instead should be determined with reference to the appended claims along with their full scope of equivalents.

What is claimed is:

1. A minimally invasive surgical instrument comprising:
   an elongate shaft having a working end and a shaft axis;
   a wrist member having a proximal portion pivotally connected to the working end to rotate relative to the working end around a pitch axis which is nonparallel to the shaft axis; and
   an end effector pivotally mounted on a distal portion of the wrist member to rotate around a wrist roll axis of the wrist member, the wrist roll axis extending between the proximal portion and the distal portion of the wrist member.

2. The instrument of claim 1 wherein the end effector is pivotally mounted to rotate relative to the wrist member around a yaw axis which is nonparallel to the wrist roll axis.

3. The instrument of claim 2 wherein the end effector includes an end effector base which is pivotally mounted on the distal portion of the wrist member to rotate around the wrist roll axis of the wrist member.

4. The instrument of claim 3 wherein the end effector includes at least one working member pivotally mounted to the end effector base to rotate around the yaw axis.

5. The instrument of claim 3 further comprising a torsion tube coupled with the end effector base and being rotatable to turn the end effector base around the wrist roll axis of the wrist member, the torsion tube extending through an interior of the elongate shaft to a proximal end opposite from the working end of the elongate shaft.

6. The instrument of claim 5 wherein the end effector includes at least one working member pivotally mounted to the end effector base to rotate around the yaw axis.

7. The instrument of claim 6 wherein the working member of the end effector is rotatable around the yaw axis by a yaw pulley-and-cable mechanism including at least one cable extending from the working member of the end effector through an interior of the torsion tube to the proximal end of the elongate shaft.

8. The instrument of claim 5 wherein the wrist member is rotatable relative to the working end around the pitch axis by a pitch pulley-and-cable mechanism including at least one cable extending from the wrist member to the proximal end of the elongate shaft through a space inside an interior of the elongate shaft and outside of the torsion tube.

9. The instrument of claim 5 wherein the torsion tube is bendable around the pitch axis with rotation of the wrist member around the pitch axis relative to the working end.

10. The instrument of claim 2 wherein the yaw axis is perpendicular to the wrist roll axis.

11. The instrument of claim 1 wherein the pitch axis is perpendicular to the shaft axis.

12. A minimally invasive surgical instrument comprising:
   an elongate shaft having a working end and a shaft axis;
   a wrist member having a proximal portion pivotally connected to the working end to rotate relative to the working end around a pitch axis which is nonparallel to the shaft axis;
   an end effector pivotally mounted on a distal portion of the wrist member to rotate around a wrist roll axis of the wrist member, the wrist roll axis extending between the proximal portion and the distal portion of the wrist member; and
   a torsion tube coupled with the end effector and being rotatable to turn the end effector around the wrist roll axis of the wrist member.

13. The instrument of claim 12 wherein the end effector includes an end effector base which is pivotally mounted on the distal portion of the wrist member and coupled with the torsion tube to be rotatable around the wrist roll axis of the wrist member.

14. The instrument of claim 13 wherein the end effector includes at least one working member pivotally mounted to the end effector base to rotate around a yaw axis which is nonparallel to the wrist roll axis.

15. The instrument of claim 14 wherein the working member of the end effector is rotatable around the yaw axis by a yaw pulley-and-cable mechanism including at least one cable extending from the working member of the end effector through an interior of the torsion tube to the proximal end of the elongate shaft.

16. The instrument of claim 12 wherein the wrist member is rotatable relative to the working end around the pitch axis by a pitch pulley-and-cable mechanism including at least one cable extending from the wrist member to the proximal end of the elongate shaft through a space inside an interior of the elongate shaft and outside of the torsion tube.

17. The instrument of claim 12 wherein the torsion tube is bendable around the pitch axis with rotation of the wrist member around the pitch axis relative to the working end.

18. A method of performing minimally invasive endoscopic surgery in a body cavity of a patient, the method comprising:
   introducing an elongate shaft having a working end into the cavity, the elongate shaft having a proximal end and a shaft axis between the working end and the proximal end;
   rotating a wrist member pivotally coupled with the working end relative to the working end, the wrist member having a wrist roll axis; and
   rotating an end effector pivotally mounted on the wrist member around the wrist roll axis to position the end effector at a desired location inside the cavity, by turning a torsion tube extending through an interior of the elongate shaft to the proximal end of the elongate shaft and being coupled with the end effector.

19. The method of claim 18 wherein the wrist member is rotated around a pitch axis which is perpendicular to at least one of the shaft axis and the wrist roll axis to change an angle between the wrist roll axis and the shaft axis.

20. The method of claim 19 wherein rotating the wrist member around the pitch axis bends the torsion tube around the pitch axis.

21. The method of claim 18 further comprising rotating at least one working member of the end effector around a yaw axis nonparallel to the wrist roll axis.

22. The method of claim 21 wherein the working member of the end effector is rotated around the yaw axis by a yaw pulley-and-cable mechanism including at least one cable extending from the working member of the end effector through an interior of the torsion tube to the proximal end of the elongate shaft.

23. The method of claim 18 wherein the wrist member is rotated around the pitch axis relative to the working end by a pitch pulley-and-cable mechanism including at least one cable extending from the wrist member to the proximal end of the elongate shaft through a space inside an interior of the elongate shaft and outside of the torsion tube.

24. The method of claim 18 further comprising rotating the elongate shaft around the shaft axis to position the end effector at the desired location inside the cavity.

* * * * *